US009237972B2

(12) United States Patent
Seidling et al.

(10) Patent No.: US 9,237,972 B2
(45) Date of Patent: Jan. 19, 2016

(54) LIQUID SURFACTANT COMPOSITIONS THAT ADHERE TO SURFACES AND SOLIDIFY AND SWELL IN THE PRESENCE OF WATER AND ARTICLES USING THE SAME

(75) Inventors: Jeffery Richard Seidling, Appleton, WI (US); Scott W. Wenzel, Neenah, WI (US); David William Koenig, Menasha, WI (US)

(73) Assignee: Kimberly-Clark Worldwide, Inc., Neenah, WA (US)

(*) Notice: Subject to any disclaimer, the term of this patent is extended or adjusted under 35 U.S.C. 154(b) by 596 days.

(21) Appl. No.: 12/336,262

(22) Filed: Dec. 16, 2008

(65) Prior Publication Data

US 2010/0152691 A1 Jun. 17, 2010

(51) Int. Cl.
| | | |
|---|---|---|
| A61F 13/51 | (2006.01) | |
| C11D 1/65 | (2006.01) | |
| A61F 13/475 | (2006.01) | |
| A61L 15/18 | (2006.01) | |
| A61L 15/48 | (2006.01) | |
| A61L 15/60 | (2006.01) | |
| A61B 19/04 | (2006.01) | |
| A61B 19/08 | (2006.01) | |

(52) U.S. Cl.
CPC ............... *A61F 13/475* (2013.01); *A61L 15/18* (2013.01); *A61L 15/48* (2013.01); *A61L 15/60* (2013.01); *C11D 1/65* (2013.01); *A61B 19/04* (2013.01); *A61B 19/081* (2013.01); *A61B 19/088* (2013.01)

(58) Field of Classification Search
None
See application file for complete search history.

(56) References Cited

U.S. PATENT DOCUMENTS

| | | | | |
|---|---|---|---|---|
| 3,325,414 A | * | 6/1967 | Inamorato | C11D 1/62 510/330 |
| 3,996,146 A | * | 12/1976 | Tarasov et al. | 510/124 |
| 4,154,542 A | * | 5/1979 | Rasmason | 401/7 |
| 4,321,165 A | * | 3/1982 | Smith et al. | 510/350 |
| 4,552,685 A | * | 11/1985 | Kernstock et al. | 510/535 |
| 4,581,042 A | * | 4/1986 | Willmore | 51/293 |
| 4,772,427 A | * | 9/1988 | Dawson et al. | 510/158 |
| 4,789,496 A | * | 12/1988 | Broze et al. | 510/338 |
| 4,954,280 A | * | 9/1990 | Elliott et al. | 510/222 |
| 5,004,557 A | * | 4/1991 | Nagarajan et al. | 510/337 |
| 5,034,218 A | * | 7/1991 | Duvel | 424/70.12 |
| 5,147,574 A | * | 9/1992 | MacGilp et al. | 510/159 |
| 5,202,045 A | * | 4/1993 | Karpusiewicz et al. | 510/277 |
| 5,246,613 A | | 9/1993 | Gilbert et al. | |
| 5,292,795 A | * | 3/1994 | Southwick et al. | 524/562 |
| 5,306,434 A | * | 4/1994 | Schueller et al. | 424/70.12 |
| 5,472,455 A | * | 12/1995 | Mehreteab et al. | 8/137 |
| 5,571,516 A | | 11/1996 | Tezuka et al. | |

(Continued)

FOREIGN PATENT DOCUMENTS

| | | |
|---|---|---|
| EP | 0 692 248 A1 | 1/1996 |
| RU | 2 066 143 C1 | 9/1996 |

(Continued)

*Primary Examiner* — Paula L. Craig
(74) *Attorney, Agent, or Firm* — Kimberly-Clark Worldwide, Inc.

(57) ABSTRACT

A liquid surfactant composition includes at least one anionic surfactant and at least one cationic surfactant. The combination of surfactants is formulated to provide a liquid composition that swells in the presence of water or body fluids, becomes a moldable solid in the presence of an excess of water, and adheres to surfaces. In addition, the liquid surfactant composition may be incorporated into or onto a substrate, such as an absorbent substrate, a fabric or cloth substrate, a tissue substrate, or a protective garment substrate.

18 Claims, 3 Drawing Sheets

(56) References Cited

U.S. PATENT DOCUMENTS

| | | | | |
|---|---|---|---|---|
| 5,679,330 A | * | 10/1997 | Matsuo et al. | 424/70.19 |
| 5,716,703 A | | 2/1998 | Payne | |
| 5,720,964 A | * | 2/1998 | Murray | 424/401 |
| 5,814,596 A | * | 9/1998 | Aquad et al. | 510/444 |
| 5,839,842 A | * | 11/1998 | Wanat et al. | 401/201 |
| 5,912,220 A | * | 6/1999 | Sramek et al. | 510/284 |
| 5,955,417 A | * | 9/1999 | Taylor | 510/438 |
| 5,955,418 A | | 9/1999 | Kazuta et al. | |
| 5,993,792 A | * | 11/1999 | Rath et al. | 424/70.28 |
| 6,028,043 A | | 2/2000 | Glenn, Jr. et al. | |
| 6,046,378 A | * | 4/2000 | Quincy et al. | 604/375 |
| 6,306,805 B1 | | 10/2001 | Bratescu et al. | |
| 6,340,664 B1 | * | 1/2002 | Gassenmeier et al. | 510/441 |
| 6,358,493 B1 | | 3/2002 | Birkel et al. | |
| 6,375,959 B1 | | 4/2002 | Mallo et al. | |
| 6,476,288 B1 | * | 11/2002 | VanRijswijck et al. | 604/364 |
| 6,482,422 B1 | * | 11/2002 | Paul et al. | 424/402 |
| 6,514,918 B1 | * | 2/2003 | Librizzi | 510/124 |
| 6,610,038 B1 | | 8/2003 | DiPalma et al. | |
| 6,645,510 B1 | * | 11/2003 | Coury et al. | 424/401 |
| 6,667,290 B2 | * | 12/2003 | Svendsen | 510/438 |
| 6,683,042 B1 | * | 1/2004 | Larson et al. | 510/444 |
| 6,727,196 B2 | * | 4/2004 | Yahiaoui et al. | 442/118 |
| 6,730,649 B2 | * | 5/2004 | Metcalfe | C11D 1/65 510/341 |
| 6,740,630 B2 | * | 5/2004 | Aouad et al. | 510/404 |
| 6,786,895 B1 | * | 9/2004 | Schmitz | 604/385.28 |
| 6,833,406 B1 | * | 12/2004 | Green et al. | 524/588 |
| 6,903,057 B1 | * | 6/2005 | Tsaur | 510/130 |
| 6,984,225 B2 | | 1/2006 | Raidel et al. | |
| 7,910,647 B2 | * | 3/2011 | Weide et al. | 524/379 |
| 8,551,517 B2 | * | 10/2013 | Hoffman et al. | 424/443 |
| 2001/0018409 A1 | * | 8/2001 | Singh | C11D 10/04 510/357 |
| 2002/0006890 A1 | * | 1/2002 | Sunder et al. | 510/446 |
| 2002/0041858 A1 | * | 4/2002 | Garnier et al. | 424/70.11 |
| 2002/0143304 A1 | * | 10/2002 | Elder et al. | 604/360 |
| 2003/0104018 A1 | * | 6/2003 | Bettle et al. | 424/401 |
| 2003/0171247 A1 | * | 9/2003 | Meine | C11D 11/0023 510/504 |
| 2003/0190302 A1 | * | 10/2003 | Frantz et al. | 424/70.24 |
| 2004/0009882 A1 | | 1/2004 | Elsik et al. | |
| 2004/0023832 A1 | * | 2/2004 | Gallotti | C11D 1/94 510/391 |
| 2004/0071653 A1 | * | 4/2004 | Bratescu et al. | 424/70.24 |
| 2004/0122390 A1 | * | 6/2004 | Soerens et al. | 604/367 |
| 2004/0127877 A1 | * | 7/2004 | Odorzynski et al. | 604/385.03 |
| 2004/0147891 A1 | * | 7/2004 | Sugito et al. | 604/385.01 |
| 2004/0158214 A1 | * | 8/2004 | Ponomarenko et al. | 604/367 |
| 2004/0158215 A1 | * | 8/2004 | Kasai et al. | 604/367 |
| 2004/0158216 A1 | * | 8/2004 | Kasai et al. | 604/367 |
| 2004/0204336 A1 | * | 10/2004 | Himmrich | C11D 1/65 510/504 |
| 2004/0242097 A1 | * | 12/2004 | Hasenoehrl et al. | 442/59 |
| 2004/0258649 A1 | * | 12/2004 | Peggau | C11D 1/65 424/70.21 |
| 2005/0119151 A1 | * | 6/2005 | Mayer et al. | 510/476 |
| 2005/0164896 A1 | | 7/2005 | Dabkowski et al. | |
| 2005/0215967 A1 | * | 9/2005 | Toro et al. | 604/378 |
| 2005/0227880 A1 | * | 10/2005 | Shiloach et al. | 510/130 |
| 2005/0228349 A1 | * | 10/2005 | Long et al. | 604/361 |
| 2005/0233935 A1 | | 10/2005 | Gunn et al. | |
| 2006/0036223 A1 | * | 2/2006 | Baldwin et al. | 604/360 |
| 2006/0107469 A1 | * | 5/2006 | Anthony et al. | 8/405 |
| 2006/0251602 A1 | * | 11/2006 | Goddinger et al. | 424/70.13 |
| 2006/0257281 A1 | * | 11/2006 | Weide et al. | 422/6 |
| 2007/0054832 A1 | * | 3/2007 | Hocking et al. | 510/475 |
| 2007/0295334 A1 | * | 12/2007 | Nonomura | 128/206.13 |
| 2008/0051314 A1 | * | 2/2008 | Wenzel et al. | 510/507 |
| 2008/0145267 A1 | * | 6/2008 | Do et al. | 422/5 |
| 2008/0294139 A1 | | 11/2008 | Ecker et al. | |
| 2008/0295256 A1 | | 12/2008 | Broze et al. | |
| 2008/0299199 A1 | * | 12/2008 | Bar-Shalom et al. | 424/484 |
| 2008/0317798 A1 | * | 12/2008 | Benjamin et al. | 424/402 |
| 2009/0036856 A1 | * | 2/2009 | Woltman et al. | 604/385.01 |
| 2009/0076542 A1 | * | 3/2009 | Jonn et al. | 606/215 |
| 2010/0322874 A1 | * | 12/2010 | Ribi | 424/59 |

FOREIGN PATENT DOCUMENTS

| | | |
|---|---|---|
| RU | 2 145 507 C1 | 2/2000 |
| RU | 2213548 C2 | 10/2003 |
| RU | 2 253 426 C2 | 6/2005 |
| WO | WO 96/18718 A1 | 6/1996 |
| WO | WO 02/067888 A1 | 9/2002 |
| WO | WO 03/041626 A1 | 5/2003 |
| WO | WO 03/070212 A1 | 8/2003 |
| WO | WO 2007/001341 A2 | 1/2007 |

* cited by examiner

LIQUID SURFACTANT COMPOSITIONS THAT ADHERE TO SURFACES AND SOLIDIFY AND SWELL IN THE PRESENCE OF WATER AND ARTICLES USING THE SAME

BACKGROUND

Surfactant compositions are used for a variety of purposes, including household chores, personal care, health care, and cosmetic application or removal.

For example, the benefits of proper hand washing are well known. This is particularly apt after using the restroom. However, despite the known benefits, not all people regularly and properly wash their hands. This is particularly true with children who may not appreciate the benefits of hand washing and may not be attended- to at wash times. As such, children may not wash their hands at all and/or may not wash their hands for an adequate amount of time and/or may not wash with an adequate cleanser. Parental supervision and coaching can improve the hand washing habits of children, but parents or caregivers are not always able to be with the child in the bathroom.

Several products have been introduced to encourage people to wash their hands for an appropriate length of time. For example, some proposed products include pads that apply a mark to the hand when soap is dispensed. The recipient of the soap and the mark are instructed to wash their hands until the mark is removed. In another example, some proposed products include a soap dispenser base designed to hold a soap dispenser. When pressure is applied to the soap dispenser, a timing means and a signal means in the base are activated. While these products may improve hand washing habits when used, they may also fail to interest children and therefore may not be used.

Additionally, many times surfactant compositions are incorporated into different substrates. For example, surfactants may be placed onto wipes, absorbent products, and tissue products. Several of these products, such as absorbent articles and protective garments, require prevention of liquid migration therethrough, especially from the sides of such products. For example, pant-like absorbent garments, such as diapers and training pants, typically include a pair of leg openings having an elastic portion around each leg opening, and a waist opening having an elastic portion as well. The elastic portions are intended to fit snugly around a wearer's legs to prevent leakage from the garment, yet leakage often persists. Protective garments such as face masks have also been constructed to prevent fluids from passing through.

A number of different approaches have been taken to reduce or eliminate fluid leaking from or through different substrates. For example, physical barriers, such as elasticized containment flaps, have been incorporated into such articles. The increased tension is often effective, but can result in an undesirable red marking on a wearer's skin due to increased pressure.

Thus, there remains a need for a surfactant composition that attracts and holds the attention of children and encourages them to wash their hands to ensure proper hand washing hygiene. There also exists a need to provide safe and effective ways to inhibit fluid migration within porous substrates.

SUMMARY

In response to the needs described above, the present disclosure provides a liquid surfactant composition which includes an anionic surfactant and a cationic surfactant.

In exemplary aspects, the liquid surfactant composition swells in the presence of water. Thus, the liquid surfactant composition may be used as a gasket to control movement of fluids in various articles.

In exemplary aspects, the liquid surfactant composition becomes a moldable solid when present in an excess of water to promote hand-washing.

In still other aspects, the liquid surfactant composition adheres to surfaces.

Thus, the liquid surfactant composition may be used as a household cleanser such as a toilet bowl cleaner.

In exemplary aspects, the anionic surfactant is selected from alkyl sulfates, alkyl ether sulfates, alkyl ether sulfonates, sulfate esters of an alkylphenoxy polyoxyethylene ethanol, $\alpha$-olefin sulfonates, $\beta$-alkoxy alkane sulfonates, alkylaryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and/or combinations thereof.

In exemplary aspects, the cationic surfactant is selected from fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes, and combinations thereof.

In exemplary aspects, the moldable surfactant composition can suitably contain anionic surfactants in an amount from about 50% (by weight of the composition) to about 99.9% (by weight of the composition), more typically from about 75% (by weight of the composition) to about 99.5% (by weight of the composition), and more preferably from about 90% (by weight of the composition) to about 99% (by weight of the composition).

In exemplary aspects, the moldable surfactant composition can suitably contain cationic surfactants in an amount from about 0.1% (by weight of the composition) to about 50% (by weight of the composition), more typically from about 0.5% (by weight of the composition) to about 25% (by weight of the composition), and more preferably from about 1.0% (by weight of the composition) to about 10% (by weight of the composition).

In other aspects, the liquid surfactant composition may also include antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, colorants, deodorants, fragrances, perfumes, emulsifiers, anti-foaming agents, lubricants, natural moisturizing agents, skin conditioning agents, skin protectants, skin benefit agents, solvents, solubilizing agents, suspending agents, wetting agents, humectants, preservatives, propellants, dyes and/or pigments, and combinations thereof.

In another aspect, the composition of the present disclosure may be used in combination with a product, such as a personal care product. More particularly, the liquid surfactant composition may be incorporated into or onto a substrate, such as an absorbent substrate, a fabric or cloth substrate, or a tissue substrate, among others. For example, the moldable surfactant composition may be incorporated into or onto absorbent articles, such as diapers, training pants, adult incontinence products, feminine hygiene products, and the like. In one preferred aspect, the moldable surfactant composition is a semi-liquid or liquid composition that may be used in combination with an absorbent article as a gasket to limit leakage of any exudates.

In an exemplary aspect, an absorbent personal care article having a structure with an absorbent core positioned between at least a body-facing layer and a back sheet layer, the body having a peripheral edge and a central portion is disclosed. The absorbent personal care article includes a coated area located on at least one layer of the body between the peripheral edge and the central portion of the body of the absorbent personal care article, the coated area having a semi-liquid or liquid surfactant composition as described herein that swells upon contact with water or body fluids.

In exemplary aspects, at least a portion of the coated area on the absorbent personal care article extends beyond an outer edge portion of the absorbent core.

In other exemplary aspects, the coated area is on the body-facing layer of the absorbent personal care article. In other aspects, the coated area is on the back sheet layer between the absorbent core and the peripheral edge.

In exemplary aspects, the liquid surfactant composition of the present disclosure adheres to surfaces and swells after coming in contact with water or body fluids.

In another exemplary aspect, the coated area is adjacent the entire peripheral edge of the absorbent personal care article. In other aspects, the coated area extends only adjacent the longitudinal edges of the absorbent personal care article.

In another exemplary aspect, a protective garment having a substrate layer with a body-facing layer is disclosed. At least a portion of the substrate is coated with a semi-liquid or liquid surfactant composition as described herein that is capable of adhering to a surface. In an exemplary aspect, the protective garment is selected from gowns, surgical drapes, sterile wraps, face masks, gloves and incise drapes.

BRIEF DESCRIPTION

DETAILED DESCRIPTION

Figure 1:
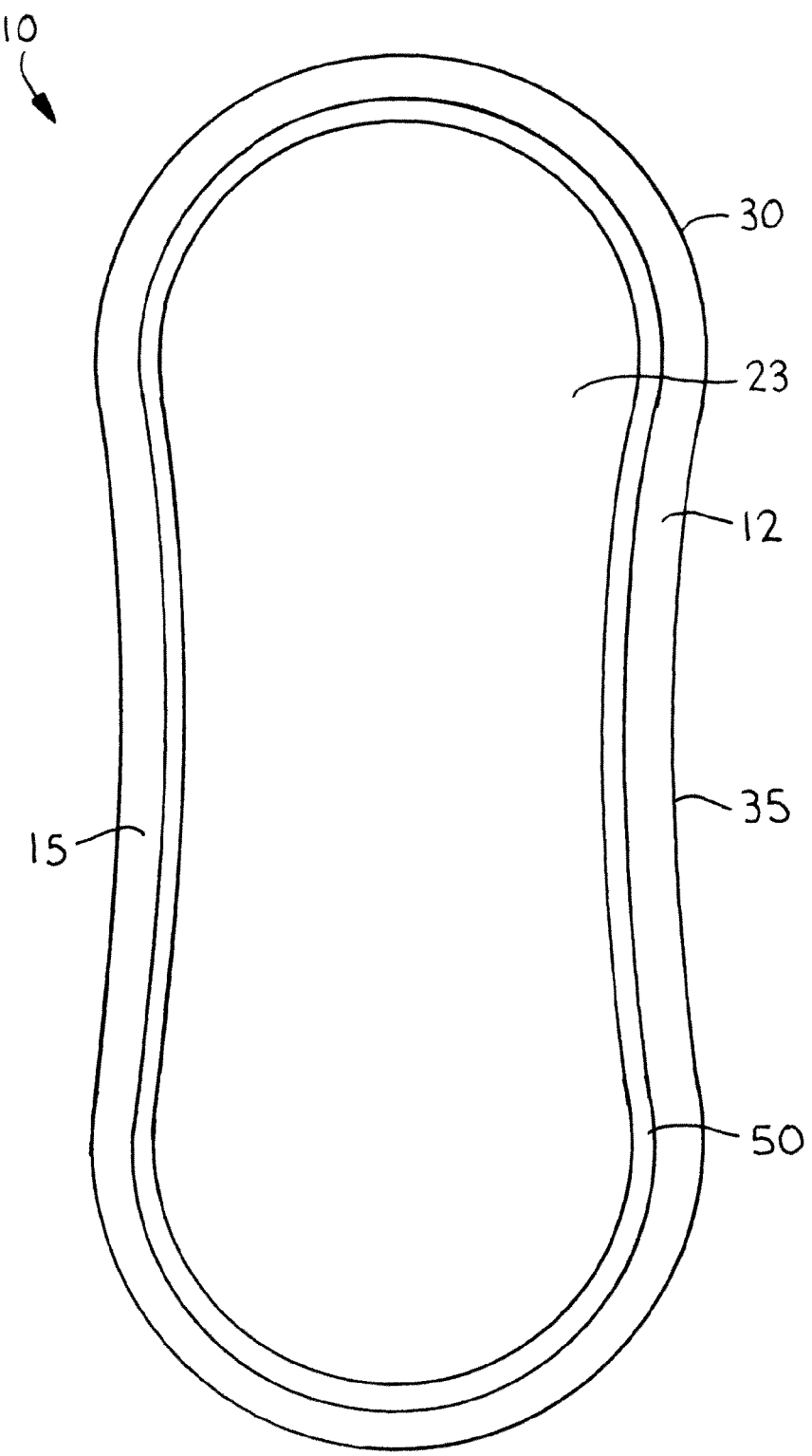
FIG. 1 illustrates a top view of an exemplary absorbent personal care article using the liquid surfactant composition.
Figure 2:
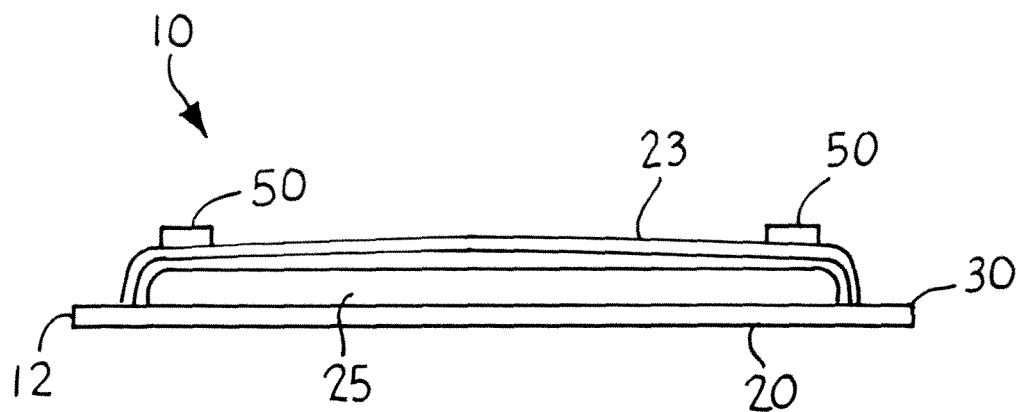
FIG. 2 illustrates a cross-sectional view of the exemplary personal care article shown in FIG. 1.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles.

As used herein, "body-facing layer" means that layer of the absorbent article which is intended to be disposed toward or placed adjacent to the body of the wearer during ordinary use. The body-facing layer includes a body-facing surface, which is intended to immediately face the body of a consumer while the product is in use. The body-facing layer also includes an internal facing surface, being opposite to the body-facing surface. The backsheet is on the opposite side of the absorbent article from the body-facing layer. The backsheet includes an outward surface (a garment facing surface) intended to face away from the wearer's body during ordinary use. The garment-facing surface is generally arranged to immediately face toward or be placed adjacent to the wearer's undergarments when the absorbent article is worn.

As used herein, the term "absorbent core" is intended to mean a configuration of an absorbent material which allows bodily fluids to be absorbed by the absorbent material.

In the following detailed description, reference is made to the accompanying drawings which form a part hereof, and in which is shown by way of illustration, specific aspects in which the disclosure may be practiced. These aspects are described in sufficient detail to enable those skilled in the art to practice the disclosed article, and it is to be understood that other aspects may be utilized and that mechanical, procedural, and other changes may be made without departing from the spirit and scope of the present disclosure. The following detailed description is, therefore, not to be taken in a limiting sense, and the scope of the present disclosure is defined only by the appended claims, along with the full scope of equivalents to which such claims are entitled.

Generally, a novel liquid surfactant composition is disclosed. In an exemplary aspect, the liquid surfactant compositions may be at least one anionic surfactant that swells in the presence of water or body fluids. In another exemplary aspect, the liquid surfactant composition includes at least one anionic surfactant and at least one cationic surfactant. The combination of surfactants is formulated to provide a liquid composition that swells when in contact with water, becomes a moldable solid when in the presence of an excess of water and adheres to surfaces. Use of the term "excess of water" herein is intended to mean a sufficient volume to be more prevalent than the volume of the surfactant composition. Unexpectedly, when large excesses of water are used in presence of the liquid surfactant composition, the liquid surfactant composition becomes a moldable solid. As used herein, a moldable solid indicates materials which are flowable under pressure having a paste-like or clay-like consistency. Moldable solid compositions include creams, ointments, gel-like materials and other similar materials.

Once the composition comes into contact with an excess of water, the liquid surfactant composition becomes a moldable solid. A consumer, or child, would then use the moldable surfactant composition, molding the clay-like substance into any desired shape. As the composition is being handled by the consumer, a portion of the surfactant composition remains on the hands of the consumer allowing for the hands to be washed.

Since the liquid surfactant composition becomes moldable, a child will more likely play and handle the composition for a longer period of time. Thus, the child will more likely wash their hands for the proper length of time, promoting better hygiene.

The liquid surfactant composition also adheres well to surfaces. Thus, the liquid surfactant composition may also be used as a household cleanser, such as a toilet bowl cleaner.

For example, the liquid surfactant composition may be included in a solution that is squirted completely around the upper rim of the toilet bowl. As the liquid seeps down the sides of the bowl it is then scrubbed with a brush around the porcelain surface. Once thoroughly scrubbed, the toilet is flushed and the stains or bacteria previously attached thereto are washed away. The liquid surfactant composition remains attached to the porcelain wall as a thin, protective coating and provides continual and long lasting cleansing action and protection through adherence of the liquid surfactant composition to the exposed bowl surface.

Exemplary anionic surfactants for use in the liquid surfactant composition include alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylaryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, or combinations thereof. Particular examples of anionic surfactants that may be utilized alone or in combination include, but are not limited to, $C_{8-22}$ alkyl sulfates, $C_{8-22}$ fatty acid salts, $C_{8-22}$ alkyl ether sulfates having one or two moles of ethoxylation, $C_{8-22}$ alkyl ether phosphates having one to three moles of ethoxylation, $C_{8-22}$ alkoyl sarcosinates, $C_{8-22}$ sulfoacetates, $C_{8-22}$ sulfosuccinates, $C_{8-22}$ alkyl diphenyl oxide disulfonates, $C_{8-22}$ alkyl carbonates, $C_{8-22}$ alpha-olefin sulfonates, methyl ester sulfonates, and blends thereof. The $C_{8-22}$ alkyl group may be a straight chain (e.g., lauryl) or branched (e.g., 2-ethylhexyl). The cation of the anionic surfactant may be an alkali metal (e.g., sodium or potassium), ammonium, $C_{1-4}$ alkylammonium (e.g., mono-, di-, tri-), or $C_{1-3}$ alkanolammonium (e.g., mono-, di-, tri). More specifically, such anionic surfactants may include, but are not limited to, lauryl sulfates, octyl sulfates, 2-ethylhexyl sulfates, potassium laureth phosphate, decyl sulfates, tridecyl sulfates, cocoates, lauroyl sarcosinates, lauryl sulfosuccinates, linear $C_{10}$ diphenyl oxide disulfonates, lauryl ether sulfates (1 and 2 moles ethylene oxide), myristyl sulfates, cetyl sulfates, and similar surfactants.

In a particular aspect, MIPA-laureth sulfate in the presence of the glycol carrier (Marlinat 242-90M commercially available from Sasol North America, Inc. of Houston, Tex.) is used as the anionic surfactant in the liquid surfactant composition. In another particular aspect, TIPA-laureth sulfate (Marlinat 242-90T commercially available from Sasol North America, Inc. of Houston, Tex.) in the presence of the glycol carrier is used as the anionic surfactant in the liquid surfactant composition.

In exemplary aspects, the liquid surfactant composition can suitably have anionic surfactants in an amount from about 50% (by weight of the composition) to about 99.9% (by weight of the composition), more typically from about 75% (by weight of the composition) to about 99.9% (by weight of the composition), and more preferably from about 90% (by weight of the composition) to about 99.9% (by weight of the composition).

Exemplary cationic surfactants for use in the liquid surfactant composition include, but are not limited to, fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes and combinations thereof. Specific examples of cationic surfactants for use in the modified surfactant composition include, but are not limited to polyquaternium-7, polyquaternium-10, behentrimonium chloride, stearalkonium chloride, distearalkonium chloride, chlorhexidine digluconate, polyhexamethylene biguanide (PHMB), polyaminopropyl biguanide, cetylpyridinium chloride, benzammonium chloride, benzalkonium chloride, behentrimonium methosulfate, cetrimonium chloride, cocamidopropyl pg-dimonium chloride, guar hydroxypropyltrimonium chloride, isostearamidopropyl morpholine lactate, quaternium-80, polyquaternium-33, polyquaternium-60, polyquaternium-79, quaternium-18 hectorite, quaternium-79 hydrolyzed silk, quaternium-79 hydrolyzed soy protein, rapeseed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like.

In a particular aspect, quaternium-80 (Abil QUAT-3473 commercially available from Evonik Industries of Hopewell, Va.) is used as the cationic surfactant in the liquid surfactant composition.

In exemplary aspects, the liquid surfactant composition can suitably have cationic surfactants in an amount from about 0.1% (by weight of the composition) to about 50% (by weight of the composition), more typically from about 0.1% (by weight of the composition) to about 25% (by weight of the composition), and more preferably from about 0.1% (by weight of the composition) to about 10% (by weight of the composition).

The compositions may further have additional agents that impart a beneficial effect on skin or hair and/or further act to improve the aesthetic feel of the liquid surfactant compositions described herein. Examples of suitable skin benefit agents include emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Thus, in one aspect, the compositions may further optionally include one or more emollient, which typically acts to soften, soothe, and otherwise lubricate and/or moisturize the skin. Suitable emollients that can be incorporated into the compositions include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

Suitable esters as emollients could include, but not be limited to, cetyl palmitate, stearyl palmitate, cetyl stearate, isopropyl laurate, isopropyl myristate, isopropyl palmitate, and combinations thereof. The fatty alcohols as emollients could include but not be limited to octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

Sterol and sterol derivatives as emollients which are suitable for use in the compositions of the present disclosure include, but are not limited to cholesterol, sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrolanosterol, dihydrolanosteryl octyidecanoate, ergocalciferol, tall oil sterol, soy sterol acetate, lanasterol, soy sterol, avocado sterols, fatty alcohols, and combinations thereof.

The compositions of the disclosure can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, jojoba oil, maleated soybean oil, meadowfoam oil, palm kernel oil, peanut oil, rapeseed oil, grapeseed oil, safflower oil, sphingolipids, sweet almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof.

The compositions of the disclosure may optionally further comprise humectants. Examples of suitable humectants include glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin.

The compositions of the disclosure may optionally further contain moisturizers. Examples of suitable moisturizers include light hydrocarbon oil (e.g., mineral oil, isododecane, petrolatum), vegetable or natural oil (e.g., sunflower oil, olive oil, sweet almond oil, grapeseed oil, corn oil, safflower oil, shea butter, coconut oil, canola oil, castor oil, jojoba oil), hydrogenated vegetable oil (e.g., hydrogenated castor wax, hydrogenated apricot kernel oil, hydrogenated canola oil, hydrogenated jojoba oil, hydrogenated olive oil, hydrogenated sesame seed oil), fatty ester (e.g., octyldodecyl neopentanoate, stearyl stearate, isopropyl myristate, isopropyl palmitate, stearyl behenate, $C_{12}$-$C_{15}$ alkyl benzoate, butyl isostearate, cetyl caprate, cetyl caprylate, ethyl apricot kernelate, ethyl avocadate, ethylhexyl caprate/caprylate, ethylhexyl cocoate, ethylhexyl isopalmitate, isocetyl myristate, isopropyl jojobate, myristyl laurate), fatty acid (e.g., palmitic acid, stearic acid, myristic acid, oleic acid, linoleic acid, behenic acid), fatty alcohol (e.g., lauryl alcohol, cetyl alcohol, stearyl alcohol, behenyl alcohol), or combinations thereof. In one aspect, the composition may contain a fatty ester as a carrier. One example of a fatty ester is isopropyl myristate, which is available under the name TEGOSOFT M (commercially available from Evonik Industries of Hopewell, Va.).

The compositions of the disclosure may optionally further contain film formers. Examples of suitable film formers include petrolatum, emollient esters, lanolin derivatives (e.g., acetylated lanolins), superfatted oils, cyclomethicone, cyclopentasiloxane, dimethicone, natural and synthetic oils, fatty acids, fatty alcohols, waxes, synthetic and biological polymers, proteins, quaternary ammonium materials, starches, gums, cellulosics, polysaccharides, albumen, acrylates derivatives, IPDI derivatives, and the like.

The compositions of the disclosure may optionally further contain slip modifiers. Examples of suitable slip modifiers include bismuth oxychloride, iron oxide, mica, surface treated mica, ZnO, $ZrO_2$, silica, silica silyate, colloidal silica, attapulgite, sepiolite, starches (e.g., corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, bismuth oxychloride, iron oxide, aluminum oxide, silicone resin, barium sulfate, calcium carbonate, cellulose acetate, polymethyl methacrylate, polymethylsilsequioxane, talc, tetrafluoroethylene, silk powder, boron nitride, lauroyl lysine, synthetic oils, natural oils, esters, silicones, glycols, and the like.

The compositions of the disclosure may optionally further contain surface modifiers. Examples of suitable surface modifiers include silicones, quaternium materials, powders, salts, peptides, polymers, clays, and glyceryl esters.

The compositions of the disclosure may optionally further contain skin protectants. Examples of suitable skin protectants include ingredients referenced in SP monograph (21 CFR §347). Suitable skin protectants and amounts include those set forth in SP monograph, Subpart B—Active Ingredients §347.10: (a) Allantoin, 0.5% to 2%, (b) Aluminum hydroxide gel, 0.15% to 5%, (c) Calamine, 1 to 25%, (d) Cocoa butter, 50% to 100%, (e) Cod liver oil, 5% to 13.56%, in accordance with §347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1% to 30%, (h) Glycerin, 20% to 45%, (i) Hard fat, 50% to 100%, (j) Kaolin, 4% to 20%, (k) Lanolin, 12.5% to 50%, (l) Mineral oil, 50% to 100%; 30% to 35% in combination with colloidal oatmeal in accordance with §347.20(a)(4), (m) Petrolatum, 30% to 100%, (o) Sodium bicarbonate, (q) Topical starch, 10% to 98%, (r) White petrolatum, 30% to 100%, (s) Zinc acetate, 0.1% to 2%, (t) Zinc carbonate, 0.2% to 2%, (u) Zinc oxide,1 % to 25%.

The compositions of the disclosure may optionally further contain particulates. Examples of suitable particulates include bismuth oxychloride, iron oxide, mica, surface treated mica, ZnO, $ZrO_2$, silica, silica silyate, colloidal silica, attapulgite, sepiolite, starches (e.g., corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, bismuth oxychloride, iron oxide, aluminum oxide, silicone resin, barium sulfate, clays, cellulosics, calcium carbonate, cellulose acetate, polymethyl methacrylate, polymethylsilsequioxane, talc, tetrafluoroethylene, silk powder, boron nitride, lauroyl lysine, aluminum starch octenylsuccinate, and calcium starch octenylsuccinate.

The compositions of the disclosure may optionally further contain sunscreens. Examples of suitable sunscreens include aminobenzoic acid, avobenzone, cinoxate, dioxybenzone, homosalate, menthyl anthranilate, octocrylene, octinoxate, octisalate, oxybenzone, padimate O, phenylbenzimidazole sulfonic acid, sulisobenzone, titanium dioxide, trolamine salicylate, zinc oxide, and combinations thereof. Other suitable sunscreens and amounts include those approved by the FDA, as described in the Final Over-the-Counter Drug Products Monograph on Sunscreens (Federal Register, 1999:64: 27666-27693), herein incorporated by reference, as well as European Union approved sunscreens and amounts.

The compositions of the disclosure may optionally further contain additional surfactants. Examples of suitable surfactants include, for example, amphoteric surfactants, zwitterionic surfactants, non-ionic surfactants, and combinations thereof. Specific examples of suitable surfactants are known in the art and include those suitable for incorporation into personal care compositions and wipes.

The compositions of the disclosure may optionally further contain additional emulsifiers. Examples of suitable emulsifiers include nonionics such as polysorbate 20, polysorbate 80, anionics such as DEA phosphate, cationics such as behentrimonium methosulfate, and the like.

The composition of the present disclosure may additionally include adjunct components conventionally found in pharmaceutical compositions in their art-established fashion and at their art-established levels. For example, the compositions may contain additional compatible pharmaceutically active materials for combination therapy, such as antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, and combinations thereof. Other suitable additives that may be included in the compositions of the present disclosure include colorants, deodorants, fragrances, perfumes, emulsifiers, anti-foaming agents, lubricants, natural moisturizing agents, skin conditioning agents, skin protectants and other skin benefit agents (e.g., aloe vera and anti-aging ingredients such as peptides), solvents, solubilizing agents, suspending agents, wetting agents, humectants, preservatives, propellants, dyes and/or pigments, and combinations thereof.

The amounts of the optional components will depend on the cosmetic carriers used and the amounts of the cosmetic carriers in the formulations as well as the desired benefits of the composition.

In another aspect, the composition of the present disclosure may be used in combination with various products useful for household chores, personal care, health care, and cosmetic application or removal.

In one particular aspect, the liquid surfactant composition may be incorporated into or onto a substrate, such as an absorbent substrate, a fabric or cloth substrate, a tissue substrate, surgical articles, such as gowns, drapes, sterile wrap and face mask, as well as other non-surgical applications such as agriculture, mining, clean room and environmental substrates.

Polymers, and particularly thermoplastic polymers, are well suited for the formation of webs which are useful in the practice of the present invention. Nonwoven webs useful in the present invention can be made from a variety of processes including, but not limited to, air laying processes, wet laid processes, hydroentangling processes, spunbonding, meltblowing, staple fiber carding and bonding, and solution spinning.

For example, the liquid surfactant composition may be incorporated into or onto absorbent articles, such as diapers, training pants, adult incontinence products, feminine hygiene products, and the like. There exists a real consumer need for absorbent articles having improved liquid intake properties while preventing leaking in addition to providing a comfortable and flexible fit. Leakage of body fluids from absorbent personal care articles usually occurs when the article becomes saturated with absorbed fluids, or the top layer becomes saturated with fluids causing additional fluids to wick away from the center of the article towards the peripheral side edges of the absorbent article. Thus, the liquid may leak from the absorbent article and stain other clothing or cause frequent changing of the absorbent article and/or wet or dirty clothing.

In one preferred aspect, the liquid surfactant composition is a liquid composition that may be used in combination with an absorbent article as a gasket to limit leakage of any exudates. For example, the liquid surfactant composition may be coated onto peripheral edges of a body-facing layer of an absorbent personal care article to help mitigate leakage.

To gain a further understanding of an aspect of the present disclosure, attention is directed to the figures of the present specification. FIG. 1 illustrates a cross-section of an exemplary absorbent personal care article 10. In the illustrated aspect, the personal care article 10 includes a structure 12 having a liquid permeable body-facing layer 15 or cover layer, a substantially liquid impermeable back sheet layer 20 joined to the body-facing sheet layer 15 at an outer peripheral edge 30 of the structure 12, and an internal absorbent core 25 positioned and held between the body-facing layer 15 and the back sheet layer 20. As shown, the liquid permeable body-facing layer 15 and the liquid impermeable back sheet layer 20 provide exemplary exterior surfaces of the absorbent personal care article 10. The absorbent personal care article 10 may also include other components, such as liquid wicking layers, liquid intake layers, liquid distribution layers, transfer layers, and barrier layers, as well as combinations thereof. In the exemplary aspect, the body-facing layer 15 provides the absorbent personal care article 10 with a body-facing surface 23.

In some aspects, the body-facing layer 15 includes a woven fabric, a nonwoven fabric, a polymer film, a film-fabric laminate, as well as combinations thereof. Examples of a nonwoven fabric include spunbond fabric, meltblown fabric, coform fabric, a carded web, a bonded-carded-web, a bicomponent spunbond fabric as well as combinations thereof. A more particular example of a suitable material for the body-facing layer 15 includes a bonded-carded-web composed of polypropylene and polyethylene. Other examples of suitable materials include composite materials of a polymer and a nonwoven fabric material. The composite materials may be in the form of integral sheets formed by the extrusion of a polymer onto a web of spunbond material. A plurality of pores, perforations, apertures or other openings, as well as combinations thereof, which are present or formed in the body-facing layer 15, may provide the liquid-permeability. The body-facing layer 15 may retain little or no liquid in its structure and be configured to provide a comfortable and non-irritating surface next to the body of the user.

For some aspects, the back sheet 20 includes a polymeric film, a woven fabric, a nonwoven fabric, as well as combinations or composites thereof. For example, the back sheet 20 may include a polymer film laminated to a woven or nonwoven fabric. The polymer film may be composed of polyethylene, polypropylene, polyester, as well as combinations thereof. The back sheet 20 may permit passage of air and moisture vapor out of the absorbent personal care article 10 while blocking the passage of bodily liquids. An example of a suitable material includes a breathable, microporous film. Bicomponent films or other multi-component films may also be used, as well as woven and/or nonwoven fabrics which have been treated to render them liquid-impermeable. Another suitable material for the back sheet 20 includes closed cell foam materials.

Structure of the internal absorbent core 25 provides desired levels of liquid retention and storage capacity and other non-illustrated layers may provide desired levels of liquid acquisition and distribution. The internal absorbent core 25 holds a liquid, such as urine, menses, other complex biological liquid, as well as combinations thereof. The internal absorbent core 25 may include a matrix of absorbent fibers and/or absorbent particulate material, and the absorbent fiber may include natural and/or synthetic fiber. The internal absorbent core 25 may also include one or more components that modify menses or inter-menstrual liquids. The internal absorbent core 25 may also include superabsorbent material, such as a water-swellable, generally water-insoluble, hydrogel-forming polymeric absorbent material, which is capable of absorbing at least about 20, about 30, or about 60 times or more its weight in physiological saline (e.g., 0.9 wt % aqueous NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, and polyvinyl pyridine. Other suitable hydrogel-forming polymers include hydrolyzed acrylonitrile grafted starch, acrylic acid grafted starch, isobutylene maleic anhydride copolymers, and mixtures thereof. The hydrogel-forming polymers may be lightly crosslinked to render the material substantially water insoluble. Crosslinking may occur by irradiation or covalent, ionic, Van der Waals, or hydrogen bonding.

In an exemplary aspect, a liquid surfactant composition described in the present disclosure is placed onto a coated area 50 of at least one layer of the structure 12 of the absorbent personal care article 10. In an exemplary aspect, a coated area 50 is present on the body-facing layer 15 that contains the liquid surfactant composition.

Figure 4:
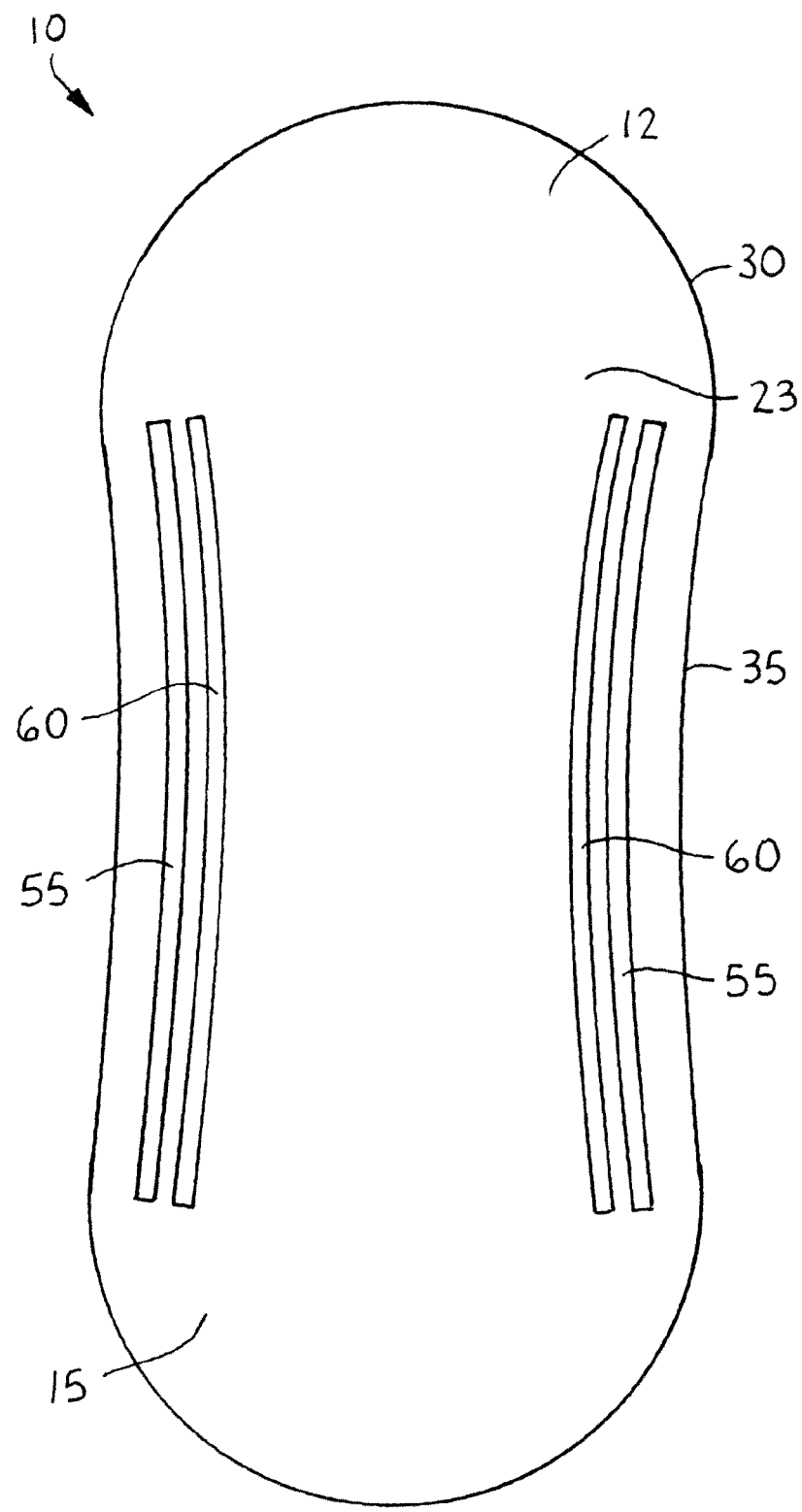
FIG. 4 illustrates another exemplary personal care article using the liquid surfactant composition.

The coated area 50 contains a liquid surfactant composition that is coated or placed onto an area adjacent the peripheral edge 30 of the structure 12 and surrounding a central region of the personal care absorbent article 10. In exemplary aspects, as shown in FIG. 1, the coated area 50 extends around the entire peripheral edge 30 of the absorbent personal care article 10. In other aspects, as illustrated in FIG. 4, the portions of the coated area 50 extend only along the longitudinal sides 35 of the absorbent personal care article 10.

The coated area 50 containing the liquid surfactant composition is capable of intercepting fluids and liquids as they travel towards the peripheral edge 30 of the personal care absorbent article 10. Liquids wicking away from the absorbent core, or flowing from the body-facing layer 15 during periods of heavier flow of exudates, will be absorbed by the swellable liquid surfactant composition. Therefore, the fluids or exudates that would potentially cause leaks are contacted by the liquid surfactant composition and the potential leakage is avoided. Additionally, the entire absorbent personal care article 10 will have increased capacity for fluid handling and storage.

In addition, the liquid surfactant composition of the present disclosure adheres to surfaces when coming in contact with water or body fluids. Thus, when the coated area 50 of the personal care absorbent article 10 is contacted with fluids during use, the body-facing layer 15 may adhere to the skin of the user. Thus, personal care absorbent article 10 provides a subsequent protection of a physical hindrance of additional flow.

In other exemplary aspects, at least a portion of the coated area 50 is placed between the end portions 65 of the absorbent core 25 and the peripheral edge 30 of the personal care absorbent article 10. Accordingly, as any fluids or exudates wick towards the ends of the personal care absorbent article 10 to move towards the peripheral edges 30, the liquids are contacted by the liquid surfactant composition and help to mitigate liquids from wicking off of the personal care absorbent article 10.

Figure 3:
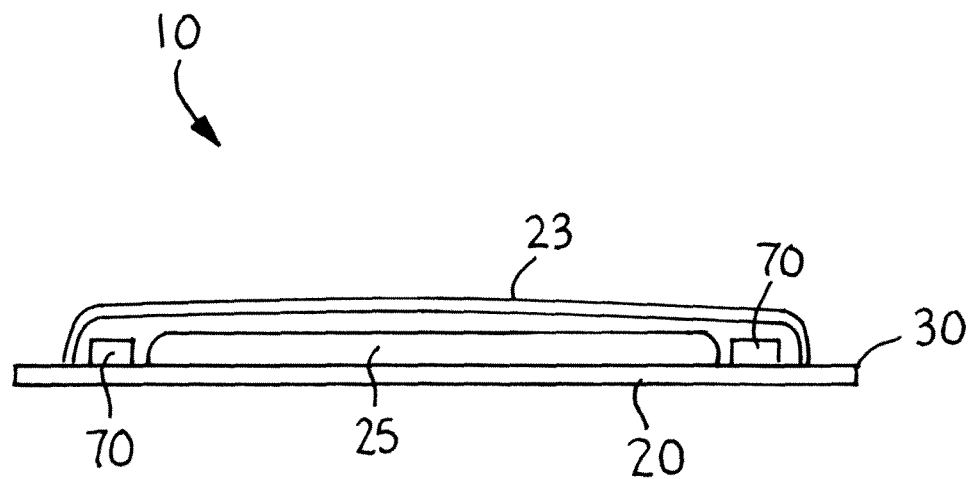
FIG. 3 illustrates a cross-sectional view of an alternative aspect of an exemplary personal care article using the liquid surfactant composition.

In another aspect, as illustrated in FIG. 3, the liquid surfactant composition may be placed onto a coated area 70 on the back sheet of the absorbent personal care article 10 adjacent the absorbent core 25. In this aspect, as the liquid wicks from the center of the absorbent core 25 towards the peripheral edge 30 of the personal care absorbent article 10, the liquids are prevented by the liquid surfactant composition from escaping the personal care absorbent article 10. The liquid surfactant composition may also be coated onto other layers such as liquid wicking layers, liquid intake layers, liquid distribution layers, transfer layers, and barrier layers, as well as combinations thereof.

In another exemplary aspect, as illustrated in FIG. 4, there exists a plurality of coated areas 55, 60 adjacent the peripheral edge 30 to further help mitigate leakage of any fluids from the peripheral edge 30 of the absorbent personal care article 10.

In another aspect, the liquid surfactant composition may be coated onto other substrates, such as protective garment articles. As is generally known, gloves, incise drapes, surgical gowns, surgical drapes, surgical face masks and sterile wraps have been designed to greatly reduce, if not prevent, the transmission through the surgical article of liquids and/or airborne contaminates. In surgical procedure environments, such liquid sources include the gown wearer's perspiration, patient liquids, such as blood and life support liquids such as plasma and saline. Examples of airborne contaminates include, but are not limited to, biological contaminates, such as bacteria, viruses and fungal spores. Often these, disposable surgical articles have largely replaced linen surgical articles. Advances in such disposable surgical articles include the formation of such articles from totally liquid repellent fabrics which prevent strike-through. In this way, biological contaminates carried by liquids are prevented from passing through such fabrics.

There are many other garment or over-garment applications, such as personal protective equipment applications, whose designers require both fabric comfort and filtration efficiency. Other personal protective equipment applications include, but are not limited to, laboratory applications, clean room applications, semi-conductor manufacturing applications, agriculture applications, mining applications, and environmental applications.

For example, a surgical mask is formed with a substrate having a body-facing layer. At least a portion of the body-facing layer is coated with a liquid surfactant composition as described herein. The substrate may be coated entirely or along the peripheral edges to provide a gasket. The liquid surfactant composition adheres to surfaces, such as skin, to optimize the gasket function of the surgical mask. As such, the liquid surfactant composition inhibits airborne or liquid biological contaminates from passing through the surgical mask into/onto the protected areas of the face. Additionally, since formulated with surfactants, the liquid surfactant composition disinfects and cleanses the area of the face protected by the mask.

As various changes could be made in the above formulations and substrates/articles without departing from the scope of the disclosure, it is intended that all matter contained in the above description shall be interpreted as illustrative and not in a limiting sense.

EXAMPLES

The following non-limiting examples are provided to further illustrate the present disclosure.

Example 1

In this example, a liquid surfactant composition was prepared. The following ingredients were used to prepare the liquid surfactant composition formulation.

| Trade Name | INCI Name | Wt. % | Grams |
|---|---|---|---|
| ABIL Quat 3474 | Quaternium-80 | 6 | 6 |
| Marlinat 242/90M | MIPA-Laureth Sulfate | 94 | 94 |

To prepare the exemplary formulation, a cationic surfactant, Quaternium-80 (commercially available from Evonik Industries of Hopewell, Va.), and an anionic surfactant, MIPA-laureth sulfate (commercially available from Sasol North America, Inc. of Houston, Tex.), were mixed together until homogeneous.

The formulation was then poured into 500 mL beaker full of tap water at room temperature. The formulation thickens and collects near the bottom of the beaker. The formulation was removed from the water and kneaded into a modeling clay-like consistency. The formulation is easily moldable into any shape that is desired by an individual handling the formulation. Additionally, the formulation is transferred onto the hands of the individual for cleaning and foaming to provide the individual with a surfactant solution to cleanse the hands.

Example 2

In this example, a liquid surfactant composition was prepared. The following ingredients were used to prepare the liquid surfactant composition formulation.

| Trade Name | INCI Name | Wt. % | Grams |
|---|---|---|---|
| ABIL Quat 3474 | Quaternium-80 | 6 | 6 |
| Marlinat 242/90T | TIPA-Laureth Sulfate | 94 | 94 |

To prepare the exemplary formulation, a cationic surfactant, Quaternium-80 (commercially available from Evonik Industries of Hopewell, VA), and an anionic surfactant, TIPA-laureth sulfate (commercially available from Sasol North America, Inc. of Houston, Tex.), were mixed together until homogeneous.

The formulation was then poured into 500 mL beaker full of tap water at room temperature. The formulation thickens and collects near the bottom of the beaker. The formulation was removed from the water and kneaded into a modeling clay-like consistency. The formulation is easily moldable into any shape that is desired by an individual handling the formulation. Additionally, the formulation sticks onto the hands of the individual for cleaning and foaming to provide the individual with a surfactant solution to cleanse the hands.

Example 3

In this example, a liquid surfactant composition was prepared. The following ingredients were used to prepare the liquid surfactant composition formulation.

| Trade Name | INCI Name | Wt. % | Grams |
|---|---|---|---|
| ABIL Quat 3474 | Quaternium-80 | 6 | 6 |
| Texapon N70 | Sodium Laureth Sulfate | 94 | 94 |

To prepare the exemplary formulation, a cationic surfactant, Quaternium-80 (commercially available from Evonik Industries of Hopewell, Va.), and an anionic surfactant, sodium laureth sulfate (commercially available from Cognis Corporation Care of Ambler, Pa.), were mixed together until homogeneous.

The formulation was then poured into 500 mL beaker full of tap water at room temperature. The formulation thickens and collects near the bottom of the beaker. The formulation was removed from the water and kneaded into a modeling clay-like consistency. The formulation is easily moldable into any shape that is desired by an individual handling the formulation. Additionally, the formulation sticks onto the hands of the individual for cleaning and foaming to provide the individual with a surfactant solution to cleanse the hands.

Example 4

In this example, a liquid surfactant composition was prepared. The following ingredients were used to prepare the liquid surfactant composition formulation.

| Trade Name | INCI Name | Wt. % | Grams |
|---|---|---|---|
| ABIL Quat 3474 | Quaternium-80 | 6 | 6 |
| Marlinat 242/90M | MIPA-Laureth Sulfate | 94 | 94 |

To prepare the exemplary formulation, a cationic surfactant, Quaternium-80 (commercially available from Evonik Industries of Hopewell, Va.), and an anionic surfactant, MIPA-laureth sulfate (commercially available from Sasol North America, Inc. of Houston, Tex.), were mixed together until homogeneous.

In addition, a feminine pad was prepared to illustrate the leakage protection of the liquid surfactant composition. First, a feminine pad was cut into 4 equal sections. The two middle sections were selected for testing. One section was treated at one peripheral edge with approximately 1 gram of the prepared liquid surfactant solution by coating the solution onto the body-facing surface in a line across the pad. The other middle section was left untreated for comparison purposes.

Both the treated and untreated sections of the feminine pad were placed into a weigh boat against a solid support at an angle of approximately 45 degrees from the support with the body-facing layer of the feminine pad facing upwards. The treated section was placed into the weigh boat with the treated portion at the floor of the weigh boat.

Then, approximately 10 grams of color-dyed water was slowly added to the center portion of the feminine pad to simulate flow of exudates onto the pad. After the liquid was added to the pad, the response by the treated and untreated section was compared. In both cases, an excess portion of the liquid moved from the center of the pad towards the edge of the pad.

The treated portion illustrated that the liquid surfactant composition swells upon contact with water helping to impede fluid migration off the surface of the pad. The treated portion illustrates that only a small portion of the water escapes past the liquid surfactant composition line. A majority of the liquid was retained above the liquid surfactant composition line in the center portion of the treated portion of the pad. In contrast, the excess liquid was allowed to move away from the center of the untreated section of the pad flowing freely to the edge of the untreated section of the pad. Thus, the liquid surfactant composition of the present disclosure provides a solution that swells upon contact with water and helps to mitigate leakage off of the pad surface.

Then, the treated and untreated sections were placed on a horizontal table surface with the body-facing layer facing up. A glass substrate was placed against the body-facing layer and pressed down. Both glass substrates were then raised several centimeters off the table surface. The treated section of the feminine pad adhered to the glass substrate and was lifted off of the table surface. In contrast, the untreated portion remained on the table surface, not adhering to the glass substrate. Thus, the liquid surfactant composition of the present disclosure provides a solution that adheres to surfaces providing an additional protection against leakage.

It should be understood that the various aspects described herein are merely illustrative. Having described the disclosure in detail, it will be apparent that modifications and variations are possible without departing from the scope of the disclosure defined in the appended claims.

The invention claimed is:

1. A liquid surfactant composition comprising:
   an anionic surfactant, wherein the anionic surfactant is present in an amount from about 50% (by weight of the composition) to about 99.9% (by weight of the composition); and
   quaternium-80, wherein the quaternium-80 is present in the amount of 6% (by weight of the composition);
   wherein the liquid surfactant composition is waterless, swells in the presence of water or body fluids, and becomes a moldable solid when placed in an excess of water; and
   wherein the anionic surfactant is selected from the group consisting of alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylaryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and combinations thereof.

2. The liquid surfactant composition of claim 1 further comprising antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, colorants, deodorants, fragrances, perfumes, emulsifiers, anti-foaming agents, lubricants, natural moisturizing agents, skin conditioning agents, skin protectants, skin benefit agents, solvents, solubilizing agents, suspending agents, wetting agents, humectants, preservatives, propellants, dyes and/or pigments, and combinations thereof.

3. An absorbent personal care article, comprising:
   a structure having an absorbent core positioned between at least a body-facing layer and a backsheet layer, the structure having a peripheral edge and a central portion; and
   a coated area located on at least one layer of the structure between the peripheral edge and the central portion of the structure of the absorbent personal care article, the coated area comprising a liquid surfactant composition placed onto the coated area, the liquid surfactant composition comprising an anionic surfactant and a cationic surfactant, wherein the anionic surfactant is present in an amount from about 50% (by weight of the composition) to about 99.9% (by weight of the composition), the cationic surfactant is present in an amount of 6% (by weight of the composition), and wherein the liquid surfactant composition is capable of forming a precipitate and swelling when coming in contact with water or body fluids.

4. The absorbent personal care article of claim 3 wherein at least a portion of the coated area extends beyond an outer edge portion of the absorbent core.

5. The absorbent personal care article of claim 3 wherein the coated area is on the body-facing layer.

6. The absorbent personal care article of claim 3 wherein the coated area is on the backsheet layer between the absorbent core and the peripheral edge.

7. The absorbent personal care article of claim 3 wherein the liquid surfactant composition adheres to surfaces after coming in contact with water or body fluids.

8. The absorbent personal care article of claim 3 wherein the coated area is adjacent the entire peripheral edge of the absorbent personal care article.

9. The absorbent personal care article of claim 3 wherein the anionic surfactant is selected from alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylaryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and/or combinations thereof.

10. The absorbent personal care article of claim 3 wherein the cationic surfactant is selected from fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes, and combinations thereof.

11. A protective garment comprising:
    a protective garment body comprising a substrate layer having a body-facing layer, the substrate having a peripheral edge and a central portion; and
    at least a portion of the body-facing layer coated with a liquid surfactant composition, the liquid surfactant composition comprising an anionic surfactant and a cationic surfactant and wherein the liquid surfactant composition is capable of forming a precipitate and adhering to a surface, wherein the anionic surfactant is present in an amount from about 50% (by weight of the composition) to about 99.9% (by weight of the composition), and the cationic surfactant is present in an amount of 6% (by weight of the composition);
    wherein the protective garment is selected from gowns, face masks, surgical drapes, gloves, incise drapes, and sterile wraps.

12. The protective garment of claim 11 wherein liquid surfactant composition is coated between the peripheral edge and the central portion of the protective garment body.

13. The protective garment of claim 11 wherein the anionic surfactant is selected from alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylaryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and/or combinations thereof.

14. The protective garment of claim 11 wherein the cationic surfactant is selected from fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes, and combinations thereof.

15. A liquid surfactant composition comprising:
- an anionic surfactant, wherein the anionic surfactant is present in an amount from about 50% (by weight of the composition) to about 99.9% (by weight of the composition); and
- quaternium-80 in an amount of 6% (by weight of the composition);
- wherein the liquid surfactant composition adheres to surfaces and forms a precipitate when placed in excess water.

16. The liquid surfactant composition of claim 15 wherein the anionic surfactant is selected from alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylaryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and/or combinations thereof.

17. The liquid surfactant composition of claim 15 wherein the cationic surfactant is selected from fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes and combinations thereof.

18. The liquid surfactant composition of claim 15 for use as a toilet bowl cleanser.

* * * * *